United States Patent [19]

Kirmann

[11] Patent Number: Plant 6,030

[45] Date of Patent: Sep. 29, 1987

[54] GERANIUM PLANT NAMED HONEY

[75] Inventor: Wolfgang Kirmann, Langenzersdorf, Austria

[73] Assignee: Mirko Vavra, Bisamberg, Austria

[21] Appl. No.: 811,169

[22] Filed: Dec. 19, 1985

[51] Int. Cl.[4] ..... A01H 5/00

[52] U.S. Cl. ..... Plt./68

[58] Field of Search ..... Plt./68

*Primary Examiner*—Robert E. Bagwill

*Attorney, Agent, or Firm*—Schwartz, Jeffery, Schwaab, Mack, Blumenthal & Evans

[57] ABSTRACT

A geranium plant named Honey having salmon-rose flower color with dark salmon-red variegation; light green foliage; early flowering and very floriferous habit; good bud production at night temperatures up to 16° C., thus providing a long and continuous flowering period; very compact, self-branching growth habit; and, ease of propagation and good rooting habit.

2 Drawing Figures

1

The present invention comprises a new and distinct cultivar of geranium, botanically known as *Pelargonium domesticum,* and hereinafter referred to by the cultivar name Honey.

Honey is a product of a planned breeding program which had the objective of creating new geranium cultivars having compact growth habit, early flowering and long flowering period, excellent flower production, relatively small foliage and salmon-pink flower color.

Honey was originated from a hybridization made by applicant in a controlled breeding program in Bisamberg, Austria in 1980. The female parent was a cultivar designated as seedling 4/78 characterized by its small foliage, vigorous growth habit, good bud production and pale pink flower color. The male parent of Honey was a cultivar designated as seedling 5/78, having salmon-orange flower color, a compact growth habit, and relatively large foliage.

Honey was discovered and selected as one flowering plant within the progeny of the stated cross by applicant on Mar. 5, 1981 in a controlled environment in Bisamberg, Austria.

The first act of asexual reproduction of Honey was accomplished when vegetative cuttings were taken from the initial selection on Aug. 30, 1981 in a controlled environment in Bisamberg, Austria by a technician working under formulations established and supervised by Wolfgang Kirmann. Horticultural examination of selected units initiated in the spring of 1982 has demonstrated that the combination of characteristics as herein disclosed for Honey are firmly fixed and are retained through successive generations of asexual reproduction.

Honey has not been observed under all possible environmental conditions. The phenotype may vary significantly with variations in environment such as temperature, light intensity, and day length. The following observations, measurements and comparisons describe plants grown in Bisamberg, Austria under conditions which approximate those generally used in commercial practice.

The following traits have been repeatedly observed and are determined to be basic characteristics of Honey, which in combination distinguish this geranium as a new and distinct cultivar.

2

1. Salmon-rose flower color, variegated with deep salmon-red; under surface of petals are pale salmon-pink.
2. Early flowering and very floriferous.
3. Light green foliage.
4. Very compact, self-branching growth habit.
5. Propagates well with very good rooting habit.
6. Honey is unique with regard to the combined features of compactness, continuous flowering, floriferous habit, and salmon-rose flower color.
7. Buds are produced under normal greenhouse conditions (5000 Lux for 16 hours per day) at 14°-16° C. This is well above the cooler temperatures required for previous *domesticum* varieties. In addition, plants flowered indoors can be transplanted outdoors and will continue blooming at night temperatures as high as 16° C. Known *domesticum* cultivars will produce buds outdoors only at night temperatures of 10° C. or lower.

Of the many commercial cultivars known to the present inventor, the most similar in comparison to Honey is Rapture, an unpatented but commercial cultivar. In comparison to Rapture, Honey has a more compact growth habit, larger foliage, flowers earlier, and has a deeper and more intense flower color.

The accompanying photographic drawings show typical flower and foliage characteristics of Honey, with colors being as true as possible with illustrations of this type.

Sheet 1 is a perspective view of a potted plant of Honey.

Sheet 2 is a black and white print showing the upper surface of immature and mature plants of Honey.

In the following description color references are made to The Royal Horticultural Society Colour Chart (RHS). The color values were determined at 9:00 a.m. on May 23, 1985 under 35,000 Lux light intensity in a greenhouse at Hillscheid, Federal Republic of Germany.

Classification:

*Botanical.—Pelargonium domesticum.*

*Commercial.*—Commonly referred to as a "Martha Washington" geranium, and having the cultivar name Honey.

INFLORESCENCE

A. Umbel:

*Average diameter.*—Medium; 95–120 mm.
*Peduncle length.*—Normal.
*Pedicel length.*—Normal.

B. Corolla:
*Average diameter.*—65–80 mm; total inflorescence diameter within foliage.
*Form.*—Five-seven petals.
*Color (general tonality from a distance of three meters).*—Salmon-rose with salmon-red variegation.
*Color (upper surface).*—51B-C; variegated with 45A.
*Color (under surface).*—49D.

C. Bud:
*Shape.*—Round.
*Color.*—White with salmon.

D. Reproductive organs:
*Androecium.*—Yellow-red.
*Gynoecium.*—Five to eight part.

E. Spring flowering response period: Early.

F. Durability: Very good.

PLANT

A. Foliage:
*Form.*—Zygomorphic with a nectar spur.
*Margin.*—Crenate, with irregular indentations.
*Color (upper surface).*—Light green.
*Tolerance of Botrytis and soil fungi.*—Good.

B. General appearance and form:
*Internode length.*—Short.
*Branching pattern.*—Very good.
*Height.*—Compact.

I claim:

1. A new and distinct cultivar of geranium named Honey, as described and illustrated, and particularly characterized by its salmon-rose flower color with dark salmon-red variegation; light green foliage; early flowering and very floriferous habit; good bud production at night temperatures up to 16° C., thus providing a long and continuous flowering period; very compact, self-branching growth habit; and, by its ease of propagation and good rooting habit.

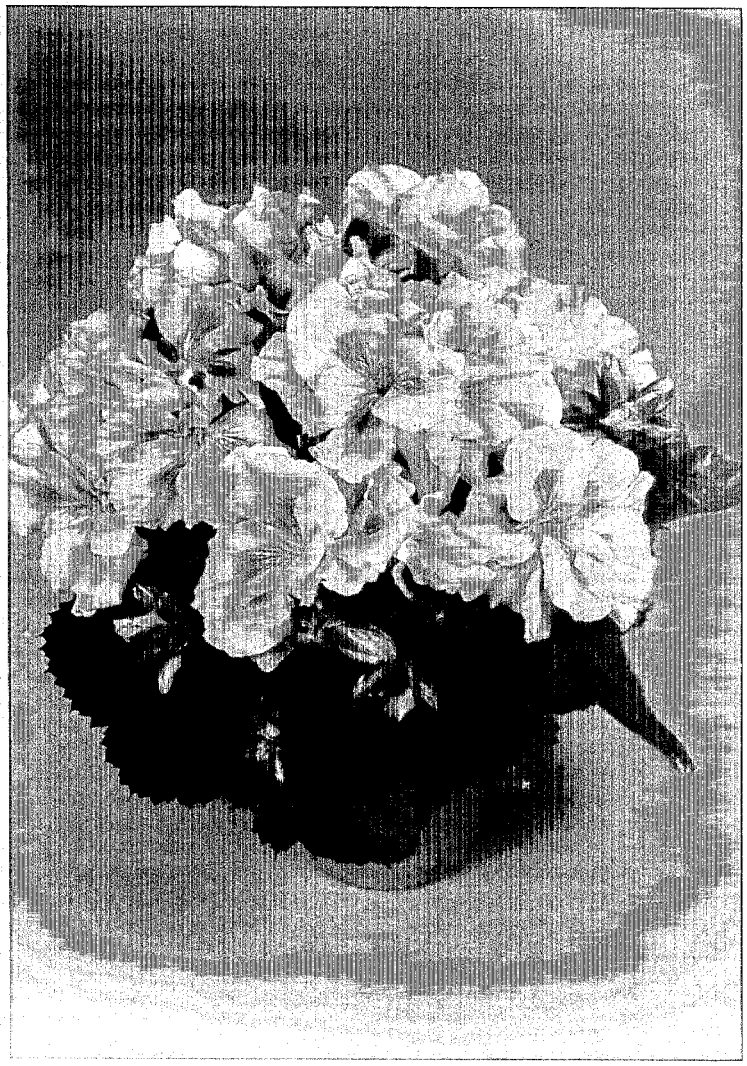

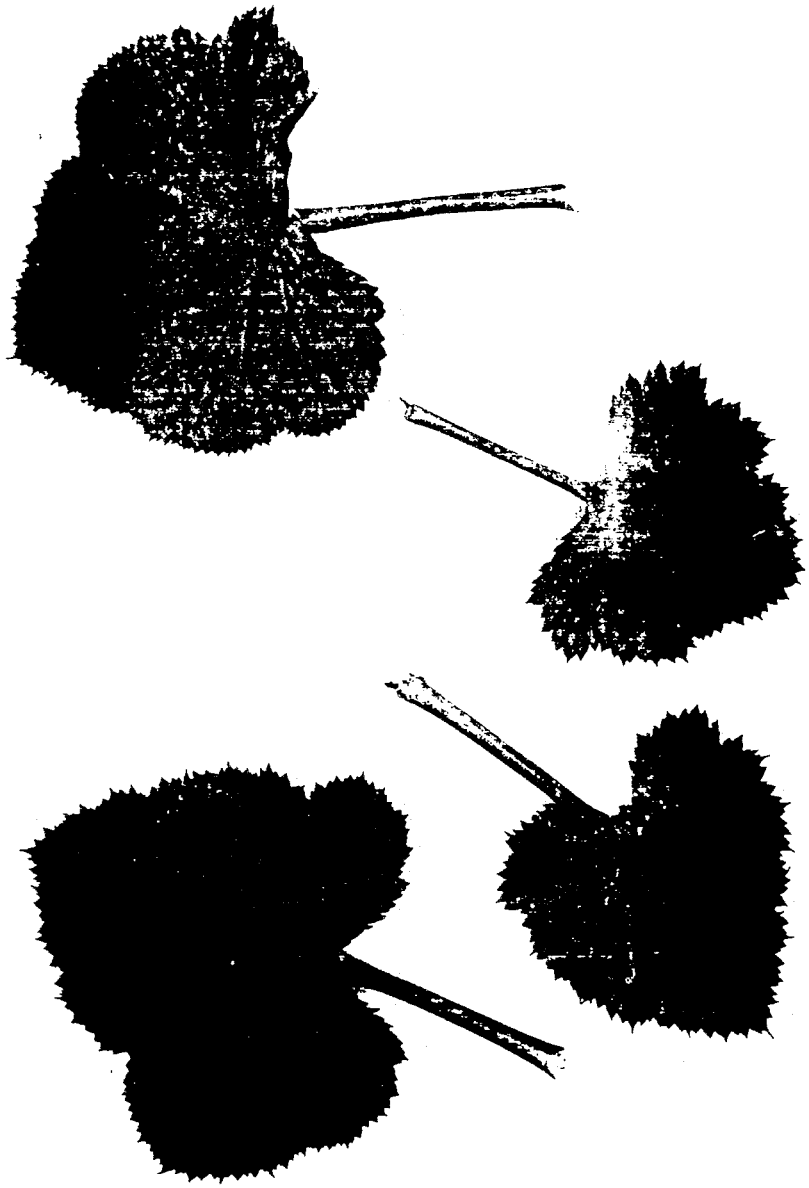

* * * * *